US012788896B2

(12) United States Patent
Magrill et al.

(10) Patent No.: US 12,788,896 B2
(45) Date of Patent: Nov. 10, 2026

(54) RECEPTACLE FOR SINGLE-HANDEDLY UNCAPPING, RECAPPING AND DISPOSING A SYRINGE'S CAP AND NEEDLE

(71) Applicant: DECAP RESEARCH AND DEVELOPMENT INCORPORATED, Richmond (CA)

(72) Inventors: Jamie Magrill, Richmond (CA); Ina Na, Vancouver (CA); Pnina Harimon Grossman, Hashmonaim (IL); Leon Trumpeldor Kalantaro, Netanya (IL)

( * ) Notice: Subject to any disclaimer, the term of this patent is extended or adjusted under 35 U.S.C. 154(b) by 484 days.

(21) Appl. No.: 18/283,649

(22) PCT Filed: Mar. 17, 2022

(86) PCT No.: PCT/CA2022/050408
§ 371 (c)(1),
(2) Date: Sep. 22, 2023

(87) PCT Pub. No.: WO2022/198306
PCT Pub. Date: Sep. 29, 2022

(65) Prior Publication Data

US 2024/0165345 A1 May 23, 2024

Related U.S. Application Data

(60) Provisional application No. 63/165,660, filed on Mar. 24, 2021.

(51) Int. Cl.
*A61M 5/32* (2006.01)

(52) U.S. Cl.
CPC ........ *A61M 5/3205* (2013.01); *A61M 5/3204* (2013.01)

(58) Field of Classification Search
CPC .............. A61M 5/3204; A61M 5/3202; A61M 5/3205; A61M 2005/3215; A61M 5/321; A61B 50/36; A61B 50/362
See application file for complete search history.

(56) References Cited

U.S. PATENT DOCUMENTS

| | | | |
|---|---|---|---|
| 7,556,623 B2 | 7/2009 | Lyman et al. | |
| 10,080,621 B2 | 9/2018 | Nakagami et al. | |
| 2017/0173272 A1* | 6/2017 | Radmand ............ | A61M 5/3276 |

FOREIGN PATENT DOCUMENTS

| | | |
|---|---|---|
| CN | 210931875 U | 7/2020 |
| CN | 214017860 U | 8/2021 |

* cited by examiner

*Primary Examiner* — Jason E Flick

(57) ABSTRACT

A receptacle for single-handedly uncapping, recapping and disposing a syringe's needle cap and needle head. The receptacle may include a receptacle unit with first and second ends and a base connected to the second end of the receptacle unit. The receptacle unit may, from its first end to its said second end, a hollow opening. The receptacle unit may, from its first end to its second end, include a wall channel. The wall channel may, at its second end be dimensioned to snugly engage the syringe's needle cap. Additionally, the wall channel may include a device for snuggly engaging a needle cap circumferential ridge and a needle head circumferential ridge.

17 Claims, 10 Drawing Sheets

RECEPTACLE FOR SINGLE-HANDEDLY UNCAPPING, RECAPPING AND DISPOSING A SYRINGE'S CAP AND NEEDLE

FIELD OF THE INVENTION

The invention relates to the field of receptacles and, particularly, to a receptacle for single-handedly uncapping, recapping and disposing a syringe's needle cap and needle head.

BACKGROUND OF THE INVENTION

Needlestick injuries are a serious occupational hazard for healthcare, veterinary and animal care workers. Although the wound from a needlestick is small and easily treated, needlestick injuries carry a high risk of infection and potential exposure to cytotoxic or pathogenic materials (HIV, Hepatitis, zoonotic diseases).

According to the CDC's National Institute for Occupational Safety and Health (NIOSH), an estimated 600,000 to 800,000 occupational needlesticks occur each year in healthcare workers. (Infection Control Resource, 2010). Up to 40% of all NSIs occur from uncapping or recapping needles (NIOSH Alert: Preventing Needlestick Injuries in Healthcare Settings, 2000). Cost of treatment for a needlestick injury is on average $600 USD, with an annual cost of ~$200 million USD in North America.

Furthermore, according to data from Estimates by Medical Care Data International, accidental needlesticks account for 80% of all occupationally acquired diseases (HIV, Hepatitis, zoonotic diseases). The transmission of blood-borne diseases is an area of great concern. Studies indicate that needlestick injuries are responsible up to 66,000 new Hep B, 16,000 new Hep C and 1,000 new HIV infections each year.

Needlesticks tend to occur during a procedure (e.g. drawing blood, drawing down drugs for injection, or administering medicine), while recapping needles, when disposing of needles, and during surgery. While a steady hand, a cooperative patient and minimal distractions can contribute to an ideal setting for avoiding needlestick injuries, needlestick injuries are still prevalent in healthcare, veterinary and animal care environments. OSHA standards recommend against recapping, however it is a frequent practice in all fields where needles are used. Therefore, when recapping or uncapping needles, it is recommended to use only one hand and to keep fingers away from the needlepoint to reduce the risk of needlestick injuries.

Accordingly, a need exists for an invention which enables users to uncap, recap, and dispose of a wide range of needle caps and needles with one hand while using the other hand to hold a subject in place.

SUMMARY OF THE INVENTION

The invention is a compact receptacle that helps users to single-handedly uncap syringes prior to use, recap them, and then safely dispose of them. The invention enables users to uncap, recap, and dispose of a wide range of needle sizes and types with one hand while using the other hand to hold a subject in place.

According to the present invention there is provided a receptacle for single-handedly uncapping, recapping and disposing a syringe's needle cap and needle head. The receptacle may include a receptacle unit with first and second ends and a base connected to the second end of the receptacle unit. The receptacle unit may, from its first end to its said second end, include a hollow opening. The receptacle unit may, from its first end to its second end, include a wall channel. The wall channel may, at its second end be dimensioned to snugly engage the syringe's needle cap. Additionally, the wall channel may include a device for snuggly engaging a needle cap circumferential ridge and a needle head circumferential ridge.

Other aspects of the invention will be appreciated by reference to the detailed description of the preferred embodiment and to the claims that follow.

BRIEF DESCRIPTION OF THE DRAWINGS

The preferred embodiment of the invention will be described by reference to the drawings thereof in which:

FIG. 5 illustrates the steps of single-handedly uncapping, recapping and disposing a syringe needle cap and needle, using a receptacle of an embodiment of the invention, wherein:

DESCRIPTION OF THE PREFERRED EMBODIMENT OF THE INVENTION

Figure 1:
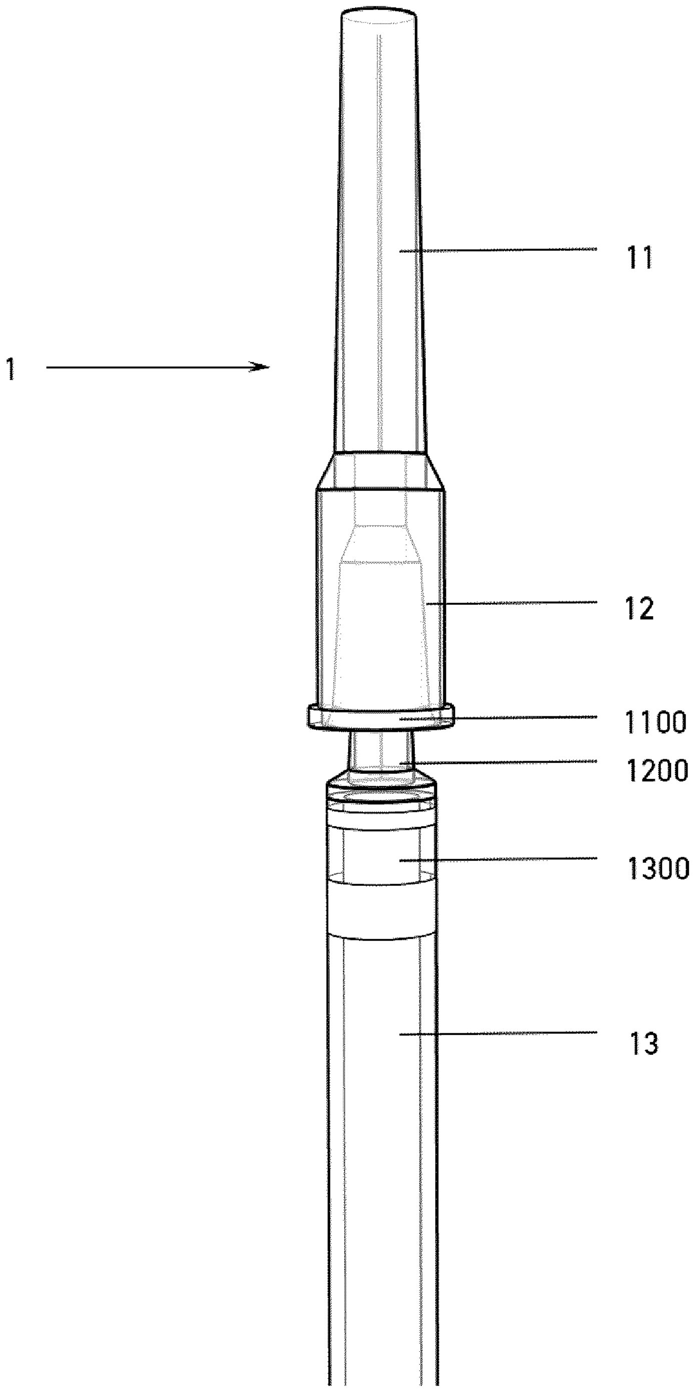
Fig.1 PRIOR ART
FIG. 1 illustrates a standard syringe; (PRIOR ART)

Referring to FIG. 1, a standard syringe 1 is depicted. The syringe 1 includes a needle cap 11, needle head 12, a syringe body 1300 and a syringe plunger 13 residing inside the syringe body. The cap 11 includes a circumferential cap ridge 1100 near its base and the needle head 12 includes a circumferential needle ridge 1200 also near its base.

Figure 2:
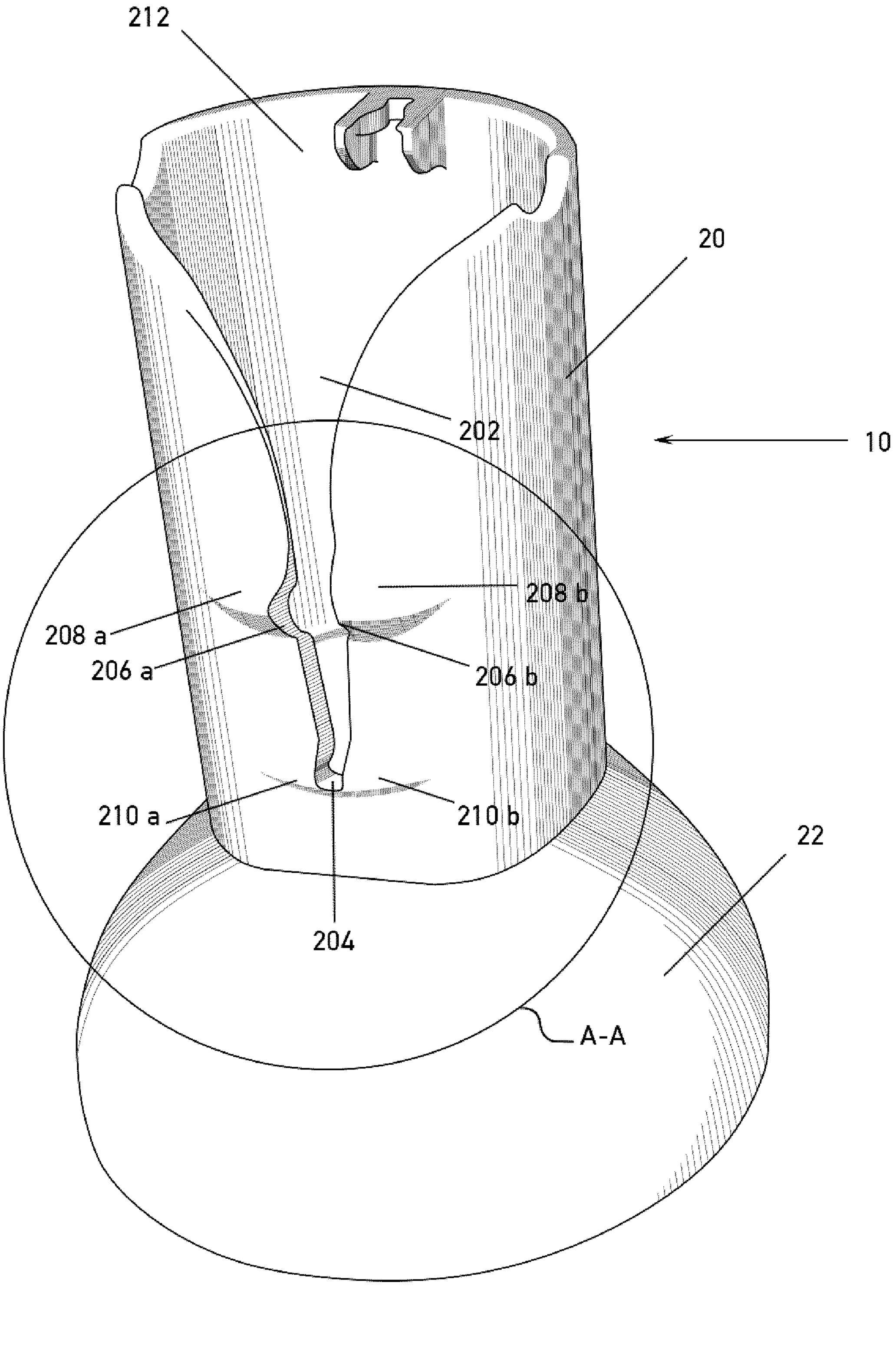
FIG. 2 is a perspective view of a receptacle for single-handedly uncapping, recapping and disposing a syringe needle cap and needle, according to an embodiment of the invention.

Referring to FIG. 2, a receptacle 10 for single-handedly uncapping, recapping and disposing the needle cap 11 and needle head 12 is shown to include a receptacle unit 20 with an opening 212 and a base 22. In one embodiment, the receptacle unit 20 is cylindrical and has a standard screw-track at the bottom allowing for it to be screwed onto the base 22. As those skilled in the art will appreciate, the receptacle unit 20 could take on other shapes and is not necessarily limited to a cylinder. Furthermore, the receptacle unit 20 could connect to the base 22 via other conventional means, or the receptacle unit 20 and the base 22 could be formed as one single body. Preferably, the base 22 is sufficiently wide support the receptacle unit and mounts to any flat surface, for example, via double-sided tape. The receptacle unit 20 may have a certain wall thickness. For example, in one embodiment where the receptacle unit is a cylinder, the thickness of the cylinder wall varies between 0.5 mm to approximately 7 mm, but as those skilled in the art will appreciate, the wall thickness may be modified for certain receptacles to accommodate various syringe sizes.

Figure 3:
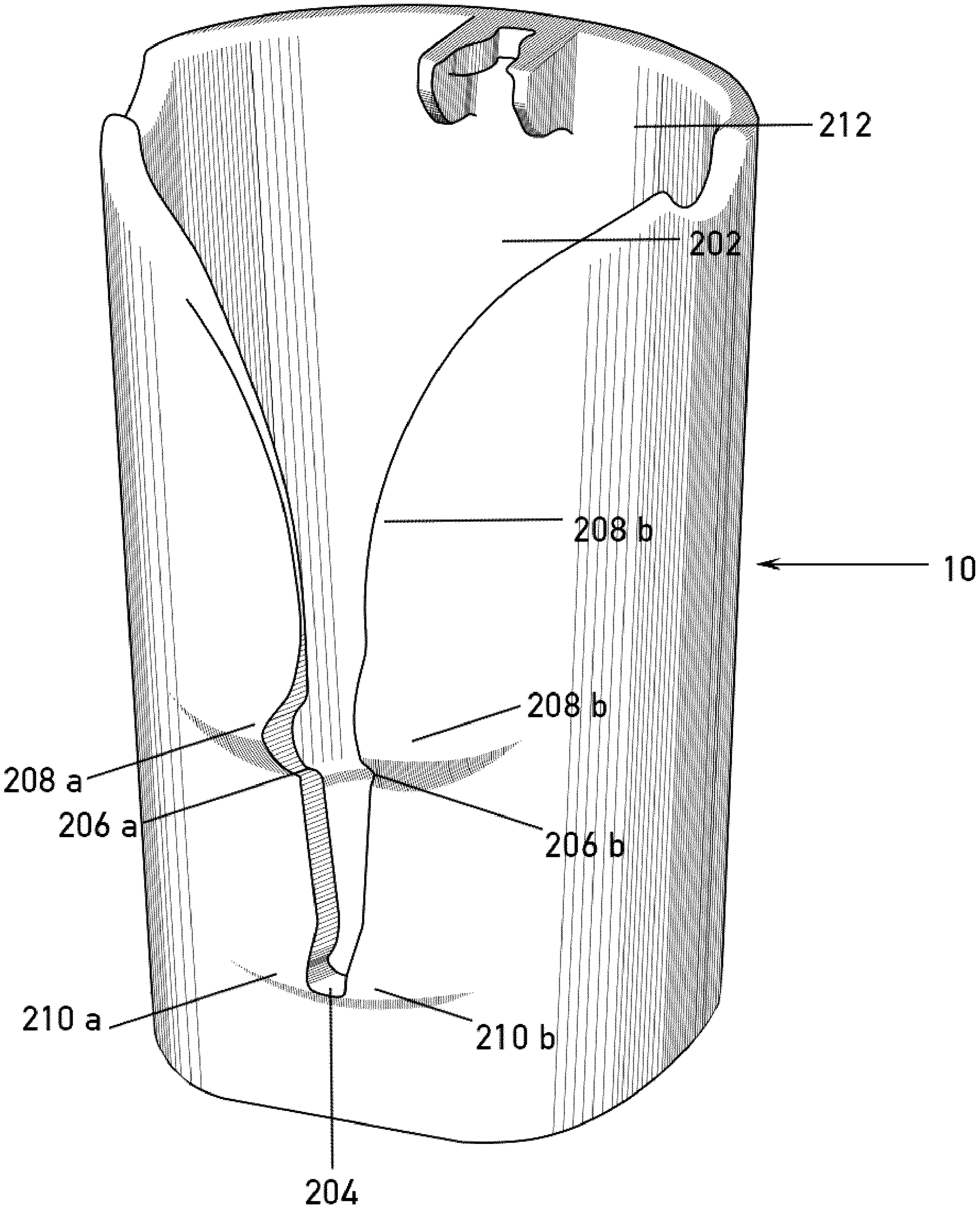
FIG. 3 is an enlarged version of the A-A circle shown in FIG. 1.
Figure 4:
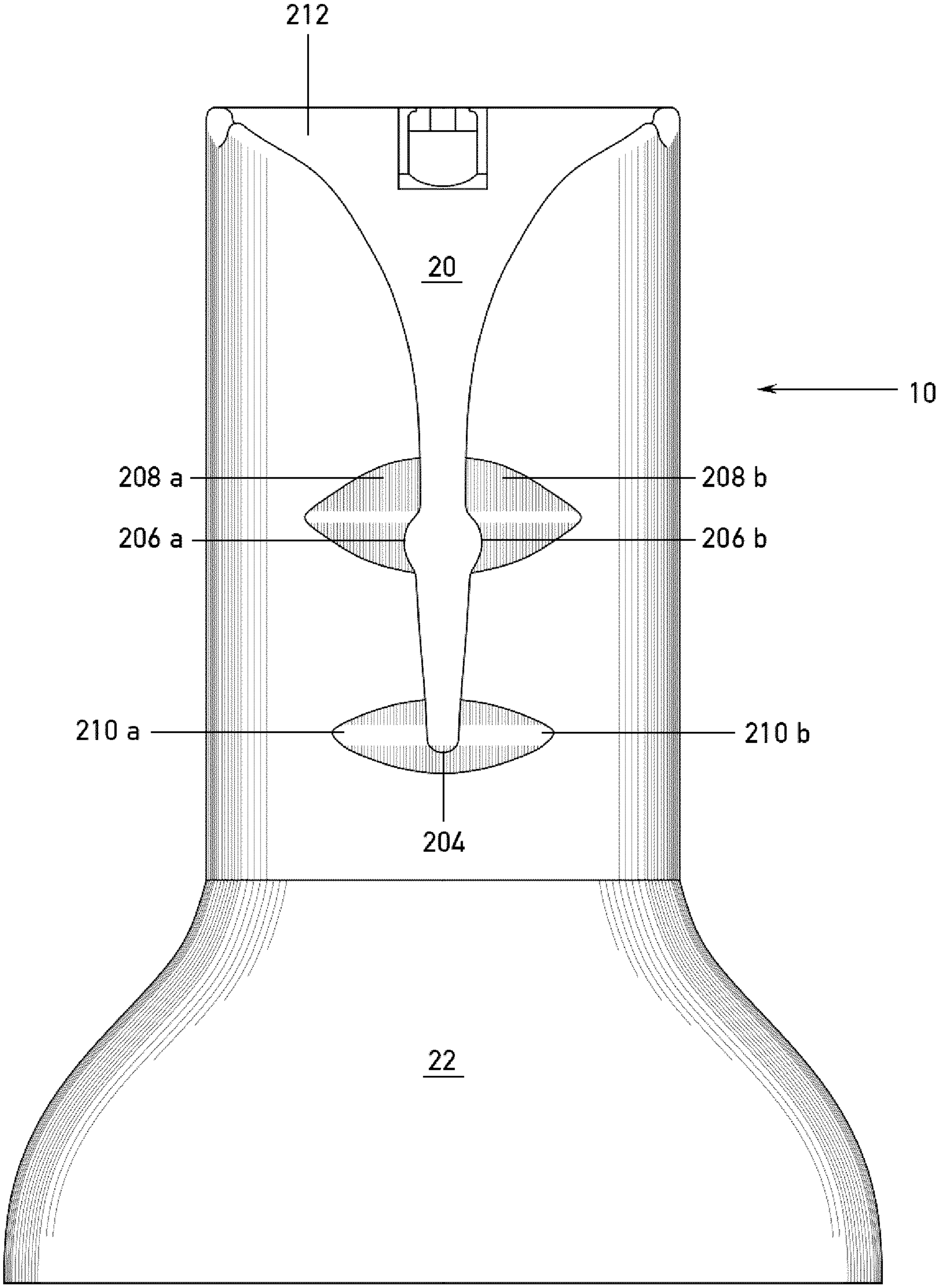
FIG. 4 is a front elevation view of the mountable receptacle shown in FIG. 1.

Referring to FIGS. 3 and 4, in one embodiment, the receptacle unit 20 includes a tapered wall channel 202 starting from the opening 212, narrowing down towards the base 22 and forming an end 204. The width of the wall channel 202 adjacent the end is dimensioned to snugly fit and hold the needle cap 11 for a user to uncap and recap the syringe as more fully discussed below. Preferably, the distance between the channel walls adjacent end 204 is approximately 3.6 mm, but as those skilled in the art will appreciate, the distance may be modified for certain receptacles to accommodate various syringe sizes. Midway along the wall channel 202 are two horizontally opposed notches 206*a* and 206*b* for disposing the needle cap 11 and needle head 12. The notches 206*a* and 206*b* are located closely enough to snuggly engage the circumferential cap ridge 1100 and the circumferential needle ridge 1200 as more fully discussed below. Preferably, the distance between the notches 206*a* and 206*b* is approximately 6 mm, but as those skilled in the art will appreciate, the distance may be modified for certain receptacles to accommodate various syringe sizes. As depicted, the contour of the wall channel 202 is a deep symmetrical Y-shape, but as those skilled in the art will appreciate, the overall appearance of the wall channel is not limited to as depicted. In some embodiments, the receptacle unit 20 could also include two sets of ridges 208*a*, 208*b*, 210*a* and 210*b* to allow for more ergonomic finger placement when a user pulls the syringe body 1300 away from the receptable 10.

Preferably, the receptacle 10 for single-handedly uncapping, recapping and disposing the syringe cap 11 and needle 12 is made from plastic, but as those skilled in the art will appreciate, it can be made from any suitable material.

Operation

Referring to FIGS. 5A-5F, a user will single-handedly uncap the syringe 1 prior to use, recap it, and then safely dispose of the cap 11 and needle 12 while using the other hand to hold a subject in place.

Figure 5A:
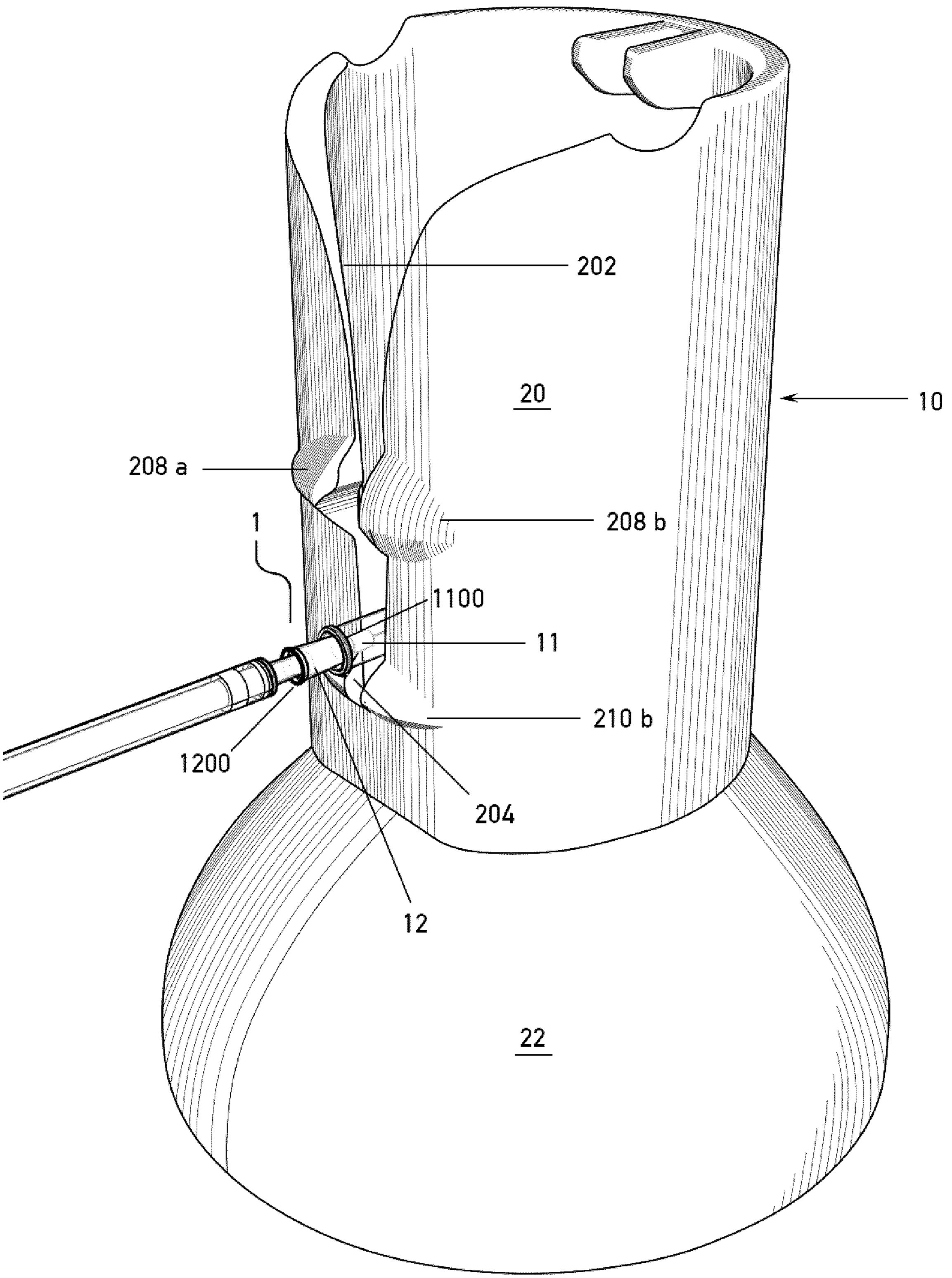
FIG. 5A illustrates the uncapping step where the needle cap is engaged with a portion of the receptacle of FIG. 1.
Figure 5B:
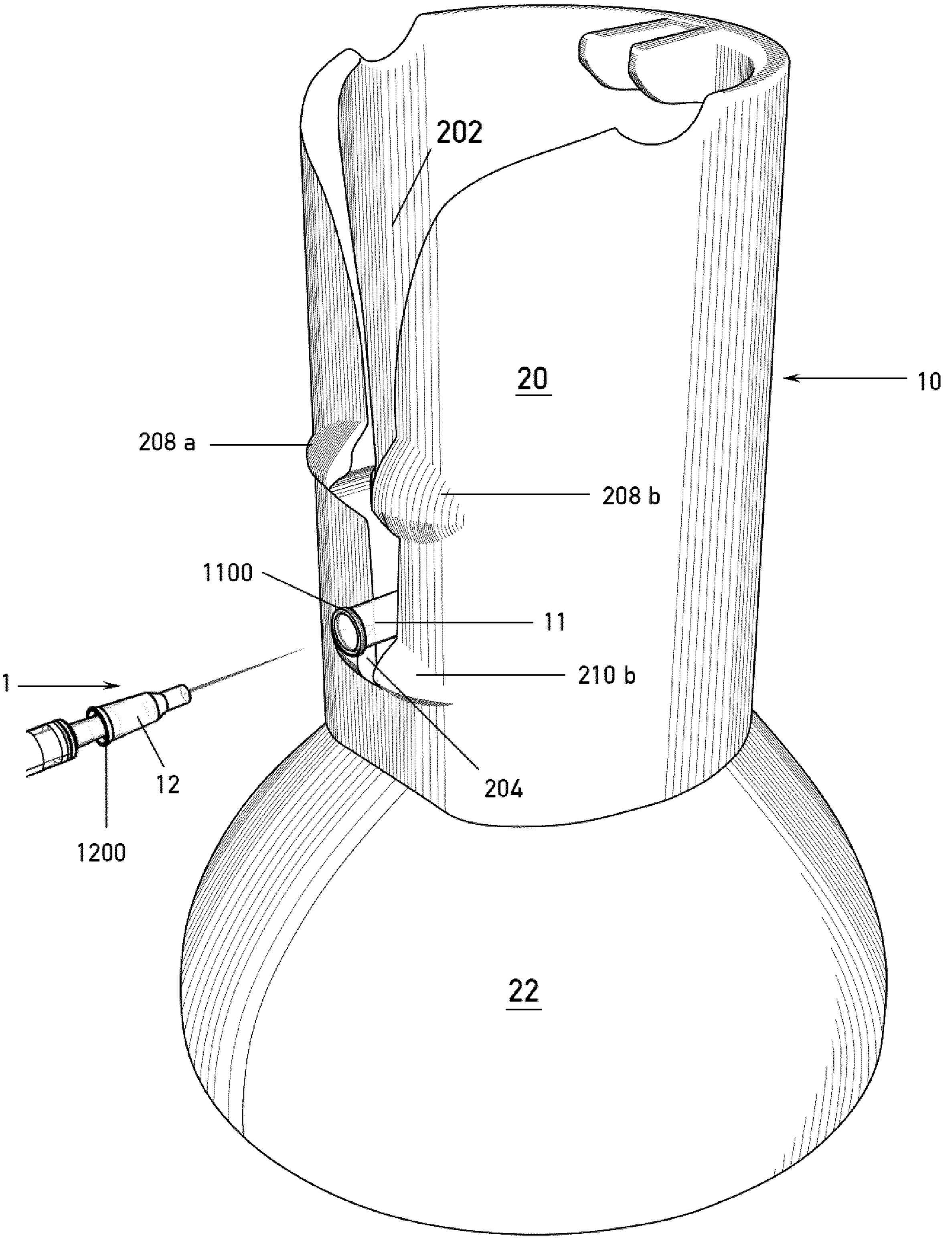
FIG. 5B illustrates the uncapping step where a syringe body is removed from the needle cap.

Referring to FIGS. 5A-5B, to uncap and recap the syringe 1, a user will hold the syringe 1 in one hand and insert the needle cap 11 part-way into the opening 212 of the receptable unit 20. As the needle cap 11 is drawn through the wall channel 202, the tapered walls of the channel, help guide the needle cap towards the end 204. The end 204, being dimensioned to engage the needle cap 11, will frictionally fit and hold the cap 11 so that a user can simply uncap the syringe 1 by apply a horizontal pulling motion on the syringe body 1300. After a user is finished using the syringe 1, the user can recap the syringe 1 by inserting the needle head 12 back into the cap 11. To remove the syringe 1, the user will then hold the needle cap 11 with the syringe body 1300 and simply pull the syringe body and head cap together and away from the receptacle 10.

Figure 5C:
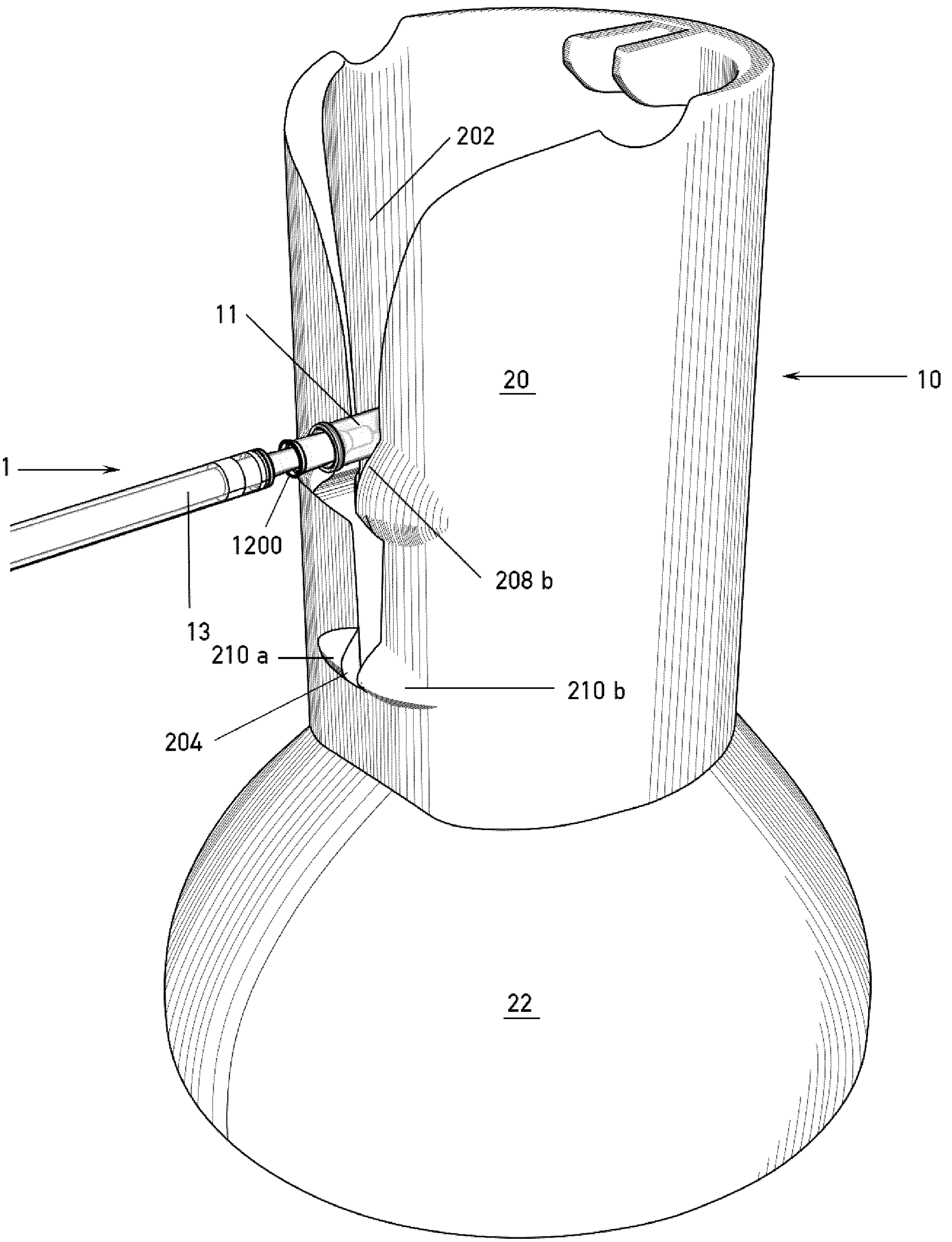
FIG. 5C illustrates the step of disposing the needle cap where the needle cap is aligned with notches on the receptacle.
Figure 5D:
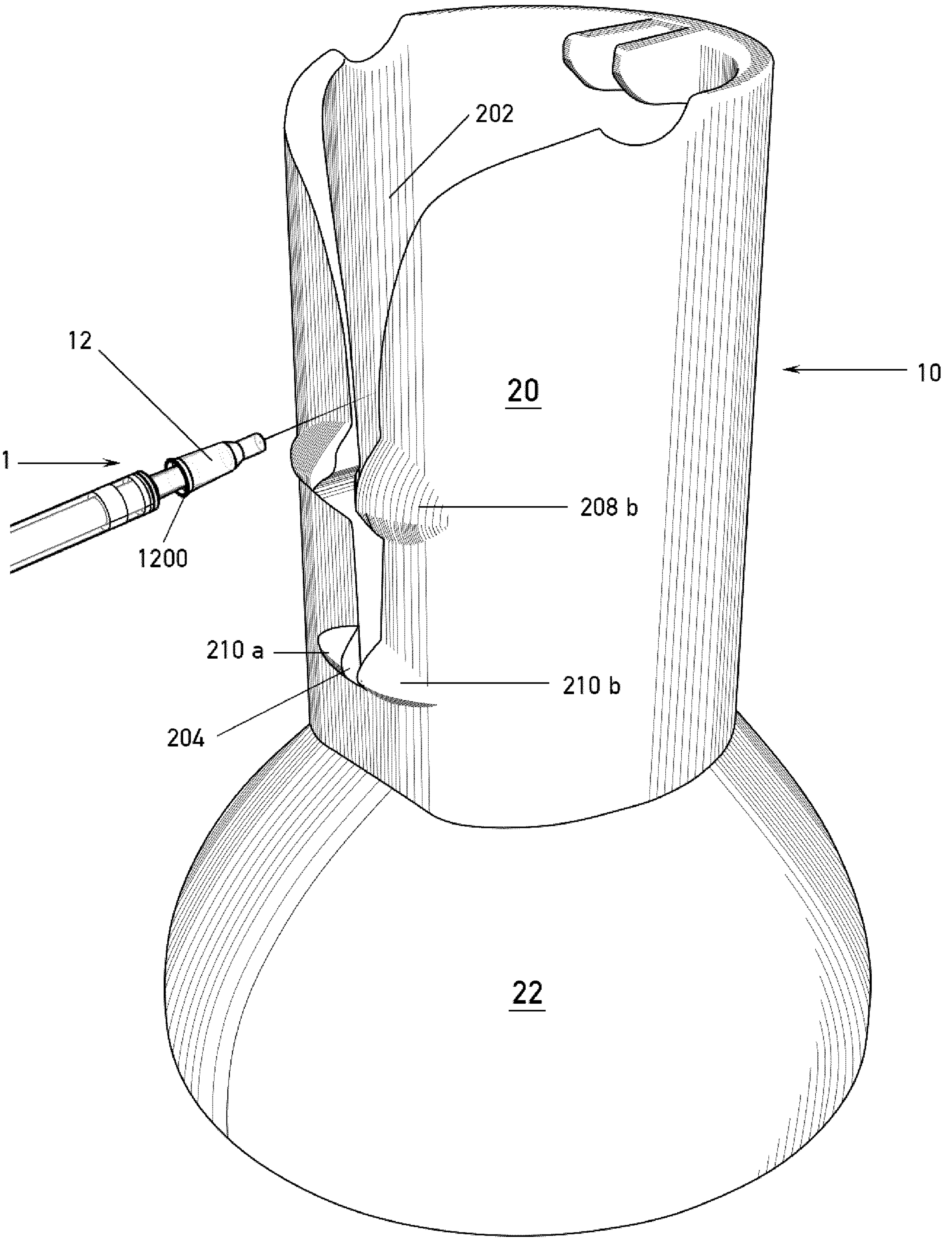
FIG. 5D illustrates the step of disposing the needle cap where the needle cap has been disposed in the receptacle.

Referring to FIGS. 5C-5D, to safely dispose the needle cap 11, the user inserts the needle cap 11 into the opening 212. This time, however, the user ensures the circumferential cap ridge 1100 is along the inside of the opening 212. As the syringe 1 is drawn through the channel 202, the tapered walls of the channel, help guide the head cap 11 towards the notches 206*a* and 206*b*. Once the needle cap 11 reaches the notches 206*a* and 206*b*, the notches snuggly engage it along the circumferential cap ridge 1100. To remove the needle cap 11, the user then simply pulls the syringe body 1300 away from the receptable 10 and the needle cap 11 falls into the receptable.

Figure 5E:
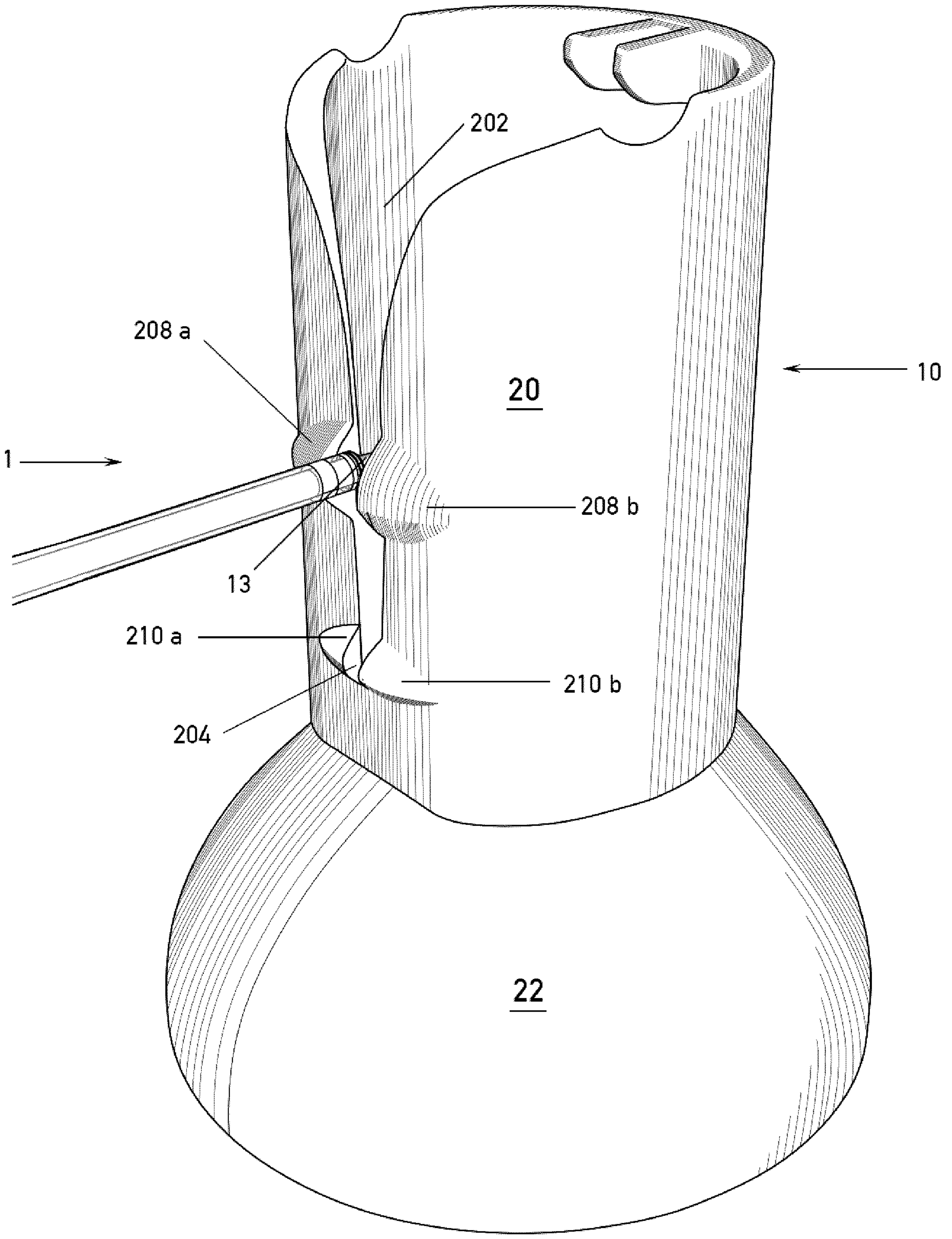
FIG. 5E illustrates the step of disposing the needle head where the needle head is aligned with the notches on the receptacle.
Figure 5F:
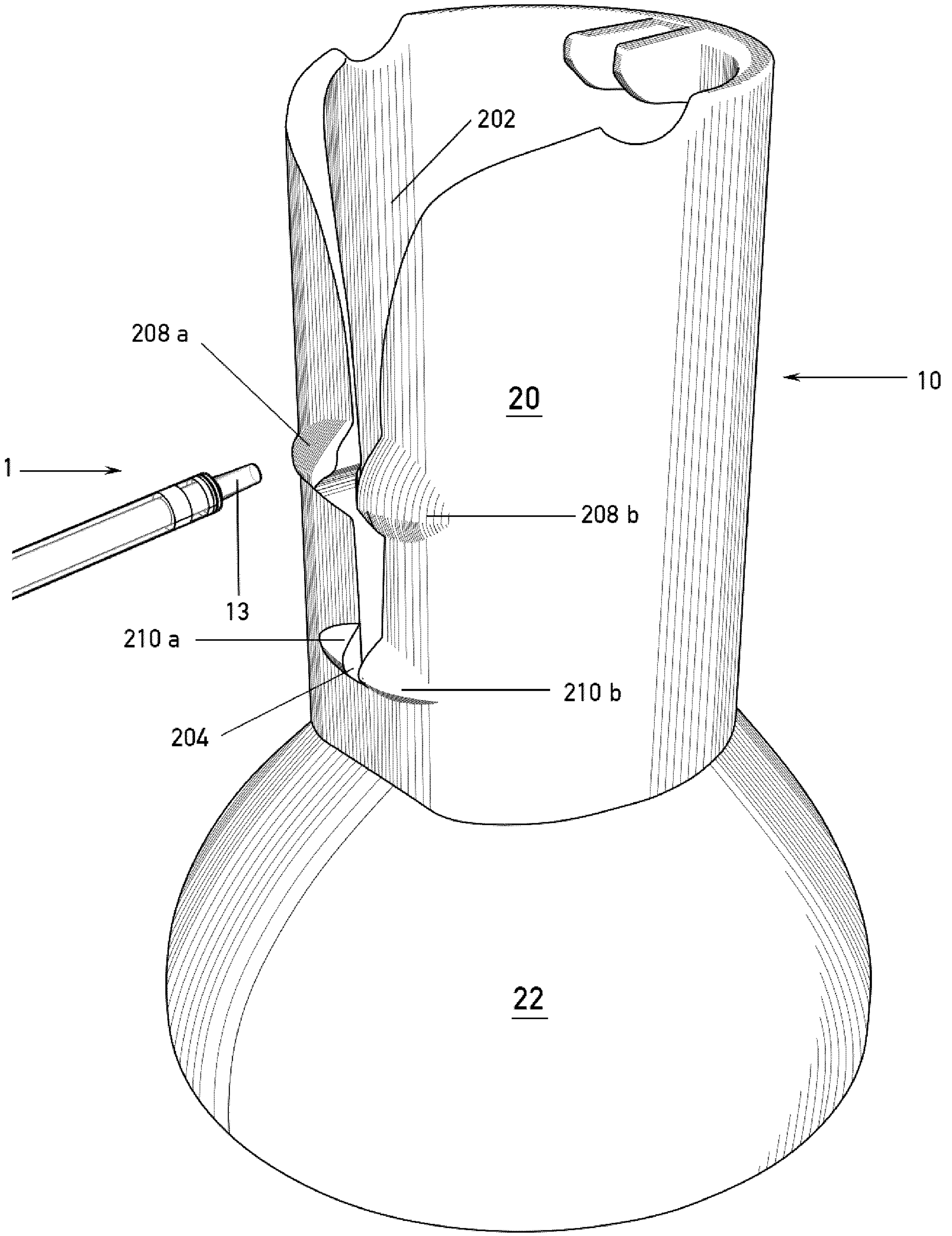
FIG. 5F illustrates the step of disposing the needle head where the needle head has been disposed in the receptacle.

Referring to FIGS. 5E-5G, to safely dispose the needle head 12, the user inserts the needle head 12 into the opening 212. This time, however, the user ensures the circumferential needle ridge 1200 is along the inside of the opening 212. As the syringe 1 is drawn through the channel 202, the tapered walls of the channel, help guide the needle head 12 towards the notches 206*a* and 206*b*. Once the needle head 12 reaches the notches 206*a* and 206*b*, the notches snuggly engage the needle head 12 along the circumferential head ridge 1200. To remove the needle head 12, the user then simply pulls the syringe body 1300 away from the receptable 10 and the needle head 12 falls into the receptable.

While embodiments of the invention have been described and illustrated, such embodiments should be considered illustrative of the invention only. The invention may include variants not described or illustrated herein in detail. Thus, the embodiments described and illustrated herein should not be considered to limit the invention as construed in accordance with the accompanying claims.

What is claimed is:

1. A receptacle for single-handedly uncapping, recapping and disposing a syringe's needle cap and needle head, comprising:

a receptacle unit with first and second ends, said receptacle unit comprising a circumferential wall, wherein said receptacle unit from said first end to said second end comprises a hollow opening;

a base connected to said second end of said receptacle unit;

wherein said circumferential wall of said receptacle unit from said first end to said second end comprises a tapered wall channel;

wherein said tapered wall channel adjacent said second end is dimensioned to engage the syringe needle cap; and wherein said wall channel is configured to engage a cap ridge of the needle cap and to also engage a needle ridge of the needle, whereby when said cap ridge is engaged with said configured wall channel and the syringe is pulled away from the needle cap, the needle cap falls into said receptable, and when the needle is engaged with said configured wall channel and the syringe is pulled away from the needle, the needle falls into said receptable.

2. The receptacle of claim 1, wherein the receptacle unit is cylindrical.

3. The receptacle of claim 1, wherein the receptacle unit and the base are formed as a single body.

4. The receptacle of claim 1, wherein the receptacle unit is removably connected to the base by a screw-track.

5. The receptacle of claim 1, wherein the tapered wall channel extends continuously from the first end of the receptacle unit toward the second end.

6. The receptacle of claim 1, wherein a width of the tapered wall channel decreases toward the second end of the receptacle unit.

7. The receptacle of claim 1, wherein the tapered wall channel terminates at an end portion dimensioned to frictionally hold the syringe needle cap.

8. The receptacle of claim 1, wherein the wall channel comprises two opposed notches positioned between the first end and the second end of the receptacle unit.

9. The receptacle of claim 8, wherein the opposed notches are dimensioned to snuggly engage the circumferential cap ridge of the needle cap.

10. The receptacle of claim 8, wherein the opposed notches are dimensioned to snuggly engage the circumferential needle ridge of the needle head.

11. The receptacle of claim 8, wherein the opposed notches are horizontally aligned with one another.

12. The receptacle of claim 1, wherein the wall channel has a generally symmetric Y-shaped contour.

13. The receptacle of claim 1, wherein the receptacle unit further comprises finger-engaging ridges formed on an exterior surface thereof.

14. The receptacle of claim 13, wherein the finger-engaging ridges are positioned adjacent the wall channel.

15. The receptacle of claim 1, wherein the base is configured to mount to a flat surface.

16. The receptacle of claim 15, wherein the base is configured for mounting by adhesive.

17. The receptacle of claim 1, wherein the receptacle is formed from plastic.

* * * * *